United States Patent
Sioufi et al.

(10) Patent No.: US 6,973,435 B1
(45) Date of Patent: Dec. 6, 2005

(54) METHOD AND SYSTEM FOR ORDERING SERVICES OR PRODUCTS, INCLUDING PRESCRIPTIONS

(76) Inventors: Habib A. Sioufi, 116 Algonquin Rd., Chestnut Hill, MA (US) 02467; Antoine Koudsi, 609 Catamaran St. #4, Foster City, CA (US) 04404

(*) Notice: Subject to any disclaimer, the term of this patent is extended or adjusted under 35 U.S.C. 154(b) by 0 days.

(21) Appl. No.: 09/352,882

(22) Filed: Jul. 13, 1999

(51) Int. Cl.[7] .............................................. G06F 17/60
(52) U.S. Cl. ...................................... 705/2; 600/300
(58) Field of Search ........................... 705/2; 368/10; 340/309.15; 600/300; 702/177; 235/385, 383, 380, 381; 128/920

(56) References Cited

U.S. PATENT DOCUMENTS

| | | | |
|---|---|---|---|
| 3,599,152 A | 8/1971 | Williams | 340/147 R |
| 3,810,102 A | 5/1974 | Parks, III et al. | 340/172.5 |
| 4,958,280 A | 9/1990 | Pauly et al. | 364/403 |
| 5,583,831 A | 12/1996 | Churchill et al. | 368/10 |
| 5,679,944 A | 10/1997 | Cusey et al. | 235/492 |
| 5,737,396 A | 4/1998 | Garcia | 379/88 |
| 5,758,095 A * | 5/1998 | Albaum et al. | 395/202 |
| 5,774,865 A | 6/1998 | Glynn | 705/2 |
| 5,805,676 A | 9/1998 | Martino | 379/93.17 |
| 5,990,782 A * | 11/1999 | Lee | 340/309.15 |
| 6,021,392 A * | 2/2000 | Lester et al. | 705/2 |
| 6,259,654 B1 * | 7/2001 | de la Huerga | 368/10 |
| 6,260,761 B1 * | 7/2001 | Peoples, Jr. | 235/462.07 |

FOREIGN PATENT DOCUMENTS

| | | | | |
|---|---|---|---|---|
| WO | WO 85/00292 | * | 1/1985 | A61M/5/14 |

OTHER PUBLICATIONS

Miller Freeman, May 5, 2001, Wasting our magic bullets, Chemist & Druggist; Issue 93033, p. 24.*
Businessline, May 9, 1999, Health & Fitness, pp. 1.*

* cited by examiner

*Primary Examiner*—Joseph Thomas
*Assistant Examiner*—Robert W. Morgan
(74) *Attorney, Agent, or Firm*—James G. O'Boyle; Mitchell B. Wasson

(57) ABSTRACT

A method and system for transmitting information included in a memory device to a remote location. The information included in the memory device could take the form of patient information as well as a prescription dosages and the remote location could be a pharmacy or a physician's office. The memory device could be fixedly attached to a drug container and a linker module would read the information contained in the memory device and automatically contact a pharmacy located at a remote location to fill a particular prescription. Information relating to the patient or the prescription which is filled can also be transferred from the remote location directly into the memory device through the linker module. In addition, the method and system can be used to order or purchase any products or services from a vendor.

11 Claims, 9 Drawing Sheets

METHOD AND SYSTEM FOR ORDERING SERVICES OR PRODUCTS, INCLUDING PRESCRIPTIONS

FIELD OF THE INVENTION

The present invention relates to a system and method of remotely ordering a prescription medication or a product or a service from a pharmacy or any vendor that dispenses prescription medications or sells the product or service.

BACKGROUND OF THE INVENTION

Virtually every day new drugs for treating various diseases or conditions are approved for use by the Food and Drug Administration (FDA). These drugs are certainly a boon to mankind but only if properly prescribed by a physician and carefully utilized by the patient. These new drugs are generally classified as being prescription or non-prescription medications. Non-prescription medications are deemed to be safe for use by the general public who can purchase these medications without a prescription. The general public is expected to follow the directions contained on the exterior of the drug's packaging or provided in a circular associated with the drug. It is presumed that if a person follows the directions associated with these types of non-prescription drugs, they would operate to relieve various conditions or symptoms without adversely affecting the user.

If the FDA believes that a particular drug must be monitored more carefully, they would be characterized as prescription drugs requiring a doctor's prescription before the drugs can be obtained. This monitoring process assures that these prescription medications would not be over-utilized by the patient. Furthermore, this monitoring process, preferably by a physician, would also endeavor to insure that a particular prescription medication would not adversely affect the patient due to a non-related condition or would not deleteriously cause a reaction with another type of medication.

Generally, once a particular prescription medication is prescribed for a patient, the doctor would write a prescription indicating the type of medication prescribed, the frequency that the medication should be taken by the patient as well as the number of refills that the patient can obtain. The patient would then take the prescription to a pharmacy or other outlet for prescription drugs.

For a refill, the patient has either to call the pharmacy ahead of time asking for a refill, or visit the pharmacy and wait for the refill. In the same case when the patient needs to renew his/her prescription, they have to call their provider and give them all the necessary information to be able to renew their prescription. There are many problems with the current system from errors in interpreting provider's orders by the pharmacist, time spent waiting for the prescription, time spent waiting on the phone, difficulty for some population and non-English speaking patients to communicate with their pharmacist and/or provider for a refill or a renewal of the prescription. All of these problems can delay patients from getting their medications on time and pose risk to the patient's well-being.

Various prior art patents have endeavored to improve this method of filling prescriptions. For example, U.S. Pat. No. 5,758,095, issued to Albaum et al illustrates an interactive medication ordering system allowing a prescriber to interact with a system utilizing a keyboard, mouse, pen-base entry or voice entry. The system would allow the prescriber to review various information relating to the patient, such as active and inactive medication prescribed for the patient. The system would accept and process medication orders and prescriptions for the patient from the prescriber which are typically comprised of drug product, dose, route of administration and frequency. This system would communicate the medication order directly to a hospital pharmacy or to an outpatient/clinic or retain pharmacy. It is however noted that this system allows a prescriber and not the patient to interact with the pharmacy. This system would also allow a prescriber access to a computer provided with the medical history of the patient, including the various drugs that the patient is now taking. While this system would in some manner streamline the drug ordering process, it's main purpose is to insure that drug interactions do not occur. Certainly, the Albaum et al patent does not contemplate that the patient would be in communication with a pharmacy and order a new prescription or to refill an old prescription.

U.S. Pat. No. 5,774,865 issued to Glynn illustrates a patient compliance and monitoring system provided with a tray holding a plurality of medication containers, each medication container having a bar code affixed to the bottom thereof. A bar code reader is fixedly attached to a positioner and electronically connected to a computer via a cable or conductor. The tray is provided with a scale allowing the computer to scan the tray each time a change in weight is sensed by the scale, which would occur each time a medicine container is placed onto the tray or retrieved from the tray. The computer may prompt the user to indicate which medication is taken and the computer would then note the date, time and dosage for any particular medication. While this patent does describe a system in which a bar code is associated with a medicine container and a reader connected to a computer can read the information on the bar code, the purpose of the system of the Glynn patent would be to insure that a patient is properly taking his or her medication. There is no teaching in the patent for a system which would communicate a prescription to a remote location, such as a pharmacy.

U.S. Pat. No. 5,737,396 issued to Garcia discusses an interactive medication data telephony system in which a data base contains information for a variety of medications and functions to receive an incoming audio communication relating to a request for information concerning a specific medication. Therefore, it can be seen that the patent to Garcia is mainly directly to a system for allowing individuals to verbally access a medical data base for particular information relating to medications and their functions.

U.S. Pat. No. 3,599,152 issued to Williams discusses a method and apparatus for distributing drugs from remotely positioned dispensing stations. A command means is located at a central pharmacy which is in telephone communications with each of a plurality of remotely positioned dispensing stations. Based upon signals initiated from the central pharmacy, medication would be dispensed at one or more of these remotely positioned dispensing stations. Typically, this system is operated by a pharmacist located at a hospital pharmacy. This pharmacist, upon receipt of a prescription from an authorized physician, would activate the system allowing the particular pharmaceuticals to be delivered to the proper patient.

While the above-noted U.S. patents describe various techniques for monitoring medications taken by patient or for determining various properties of a medication using the telephone lines, none of these patents describe a system in which the patient can order medication either initially prescribed by a physician or obtaining refills of medications initially prescribed by a physician.

SUMMARY OF THE INVENTION

The present invention overcomes the deficiencies of the prior art by utilizing a system and method in which an individual can easily obtain prescription medications. A memory device is associated with each individual prescription. The memory device can either be generated by the providers as part of the prescription or by the pharmacist. It is noted that when the memory device is generated by the provider, it can either be in addition to the written prescription, or be the prescription itself, depending on the regulations. When the provider generates the memory device, it can be used from the provider's office to call in the prescription, thus eliminating any error in interpreting the provider's orders by the pharmacist and in this way, the prescription would be ready when the patient arrives to the pharmacy. In this case, the pharmacist would keep the written prescription or copy of the information register in the memory device. The pharmacist would also register the date of the prescription and the amount dispensed in the memory device and/or any other information. The memory device can also be attached to the medication container and becomes part of the container.

In the instance when the pharmacist receives only a written prescription, the pharmacist will generate the memory device after registering all the required and appropriate information, the memory device can then be used for refills or prescription renewals, the memory device in this case also be attached to the container. This memory device can take the form of a magnetic card or can be directly attached to a container in which the medication is stored. In this embodiment, prescriptions can be easily refilled for the medications included in the container. The memory device can be provided with various information relating to the individual patient's medical history, other drugs a patient might be taking, as well as the amount of refills relating to the specific medication provided in the container. A reader is provided for reading the information included in the memory device. This reader is directly or indirectly connected to a modem, which in turn is connected to a telephone line. The telephone line is connected to a pharmacy over which medication can be ordered. If the memory device is not associated with a container, a physician or any other authorized personnel could order the prescribed medication for the patient. It is noted that information can also be transferred from the pharmacy or a physician directed to the medication which is ordered, refilled or updating the patient information in the memory.

In the same way, this can apply for any products or services, for example, the memory device and system can be used to order or reorder heating oil, food or any frequently purchased or needed services or products.

The above, and other objects, features and advantages of the present invention will become apparent from the following description read in conjunction with the accompanying drawings, in which like reference numerals designate same elements.

DETAILED DESCRIPTION OF THE INVENTION

Figure 1:
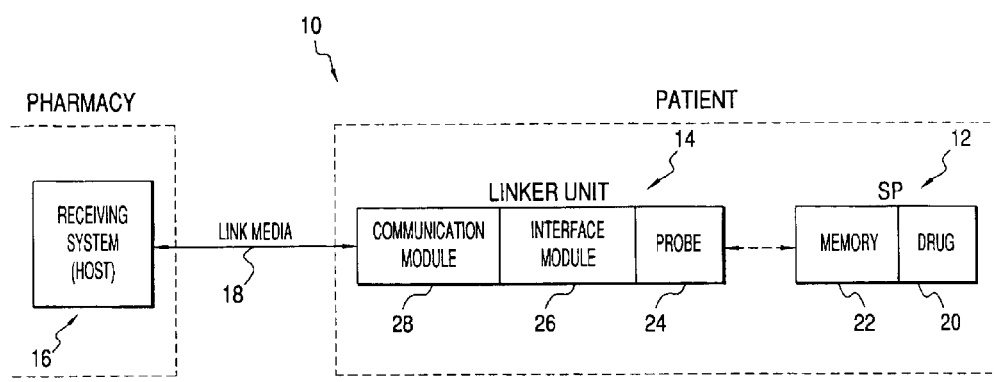
FIG. 1 is a block diagram showing the various components of the present invention.
Figure 2:
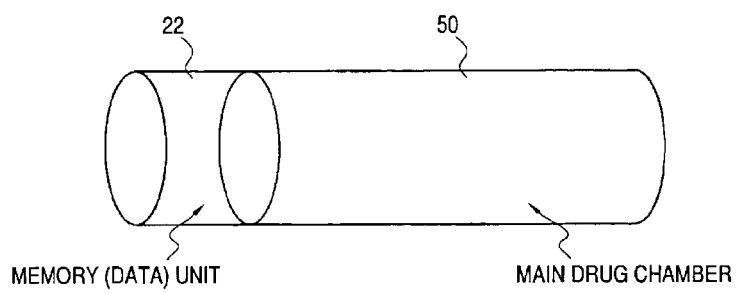
FIG. 2 is a diagram showing a memory device directly attached to a medication chamber.

The main components of the system 10 according to the present invention are illustrated in FIG. 1. These components include a device 12 storing both patient information as well as drug information, a linker module 14 and a receiving station 16. The device 12 is provided with a memory portion 22 in which this information is stored. The memory device 22 can be directly affixed to a main drug chamber 50 as illustrated in FIG. 2. However, it is noted that the memory device 22 need not be directly affixed to any drug container but can be associated with a particular prescription medication 20 or with a particular patient.

The memory device 22 can be virtually any type of solid state memory device currently on the market. Since the memory device 22 is generally designed to allow information to be read therefrom, as well as to be written therein, the memory device 22 must be capable of being read by a reader as well as interfacing with a device for changing the information within the memory. However, it is conceivable that the memory device could be issued to the patient and would have no facility for entering new information therein.

The linker unit 14 acts as a means for transferring information into and from the memory device 22. Functionally, the linker unit 14 includes a probe 24 for directly reading information contained in the memory device 22 as well as for writing additional information into the memory device. An interface module 26 is either directly connected to the probe 24 or is in communication with the probe 24 and is used to convert the data between the probe 24 and a communication module 28 such as a modem. It is noted that the interface module 26 need not be directly connected to the modem 28, but, in many instances, it would be connected to the communication module 28. The communication module 28 is used to receive and send information provided within the memory device 22 to a remote location such as a pharmacy or a physician's office noted as the receiving system or host 16.

Based upon the type of communication module 28 utilized, various links 18 would be established between the linker unit 14 and the receiving system 16. It is noted that although the present invention 10 is envisioned to connect a patient to a remote location such as the physician's office or the pharmacy, this need not be the case. Particularly if the patient is provided with a transportable memory device as will be explained in more detail herein below, this memory device may be directly presented to the receiving system 16 at which time information provided within the memory device 22 would be read out by an appropriate probe provided at the receiving system 16. This information would be processed at the receiving system 16 and additional information could be added to the memory device 22 directly at the receiving system 16.

As previously indicated, various types of memory devices 22 could be utilized according to the techniques of the present invention. For example, these memory devices are depicted in FIGS. 3A–3F which also show the connection to the linker module 14.

FIGS. 3A–3D show a system capable of writing information into a memory device as well as reading information from that device. FIGS. 3E and 3F show a system in which information is read from the memory device but is not written into the memory device.

Figure 3A:
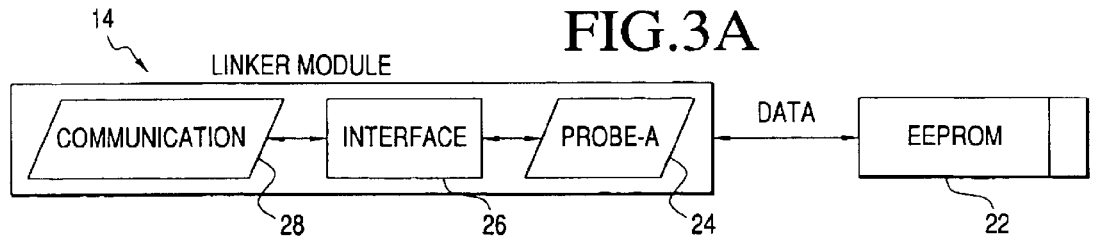
FIGS. 3A–3F are diagrams depicting the various memory devices utilized in the present invention.

For example, FIG. 3A shows a system provided with an electrical erasable programmable read-only memory (EEPROM) which would be in communication with the linker module 14. The EEPROM is an integrated circuit memory that can record data and retain the data therein indefinitely. The stored data can be erased with an electrical charge and new data would then be recorded therein.

Figure 3B:
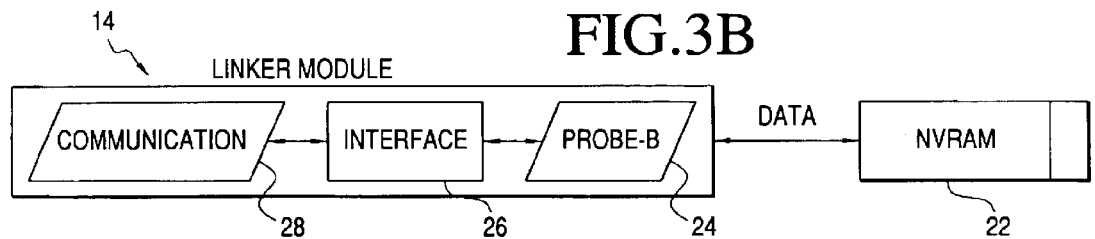

FIG. 3B shows the use of a non-volatile random access memory (NVRAM) which can also store data therein indefinitely. The stored data can be overwritten by writing to the appropriate address. The NVRAM as well as the EEPROM would require electronic reader/writers to transfer data to/from the receiving system 16. In both instances, data would be converted to an appropriate format to be processed by the communication module 22 by a specific interface module.

Figure 3C:
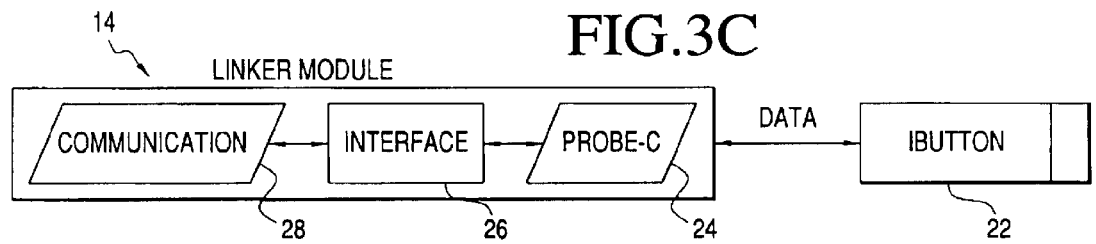
Figure 4:
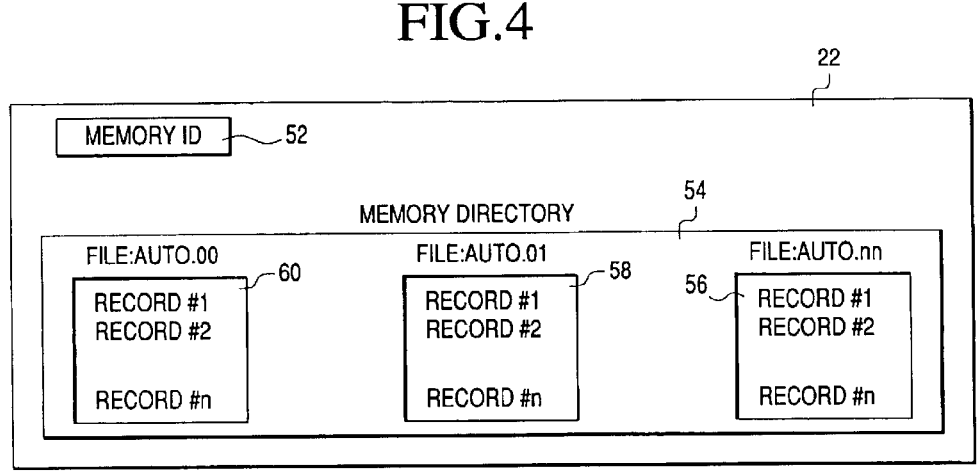
FIG. 4 is a block diagram showing a typical memory module.

FIG. 3C shows the use of a touch memory button manufactured by Dallas Semiconductor. This device would also require an electronic reader/writer to transfer data to/from the host system 16. This type of memory device is illustrated in FIG. 4. Each touch memory device contains one unique fixed memory identification 52 as well as a memory directory 54 provided with one or more data files 56, 58 and 60. Each of these data files is provided with a plurality of records. Data is stored and retrieved in the form of a record inside each of the data files. The method of reading information from and writing information into this type of memory will be discussed hereinbelow with respect to FIGS. 8 and 9.

Figure 3D:
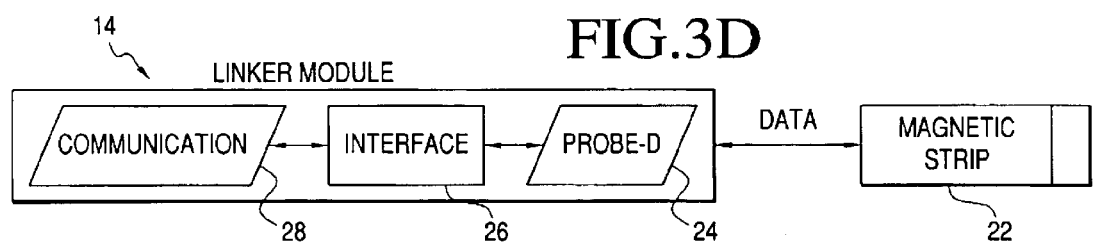
Figure 3E:
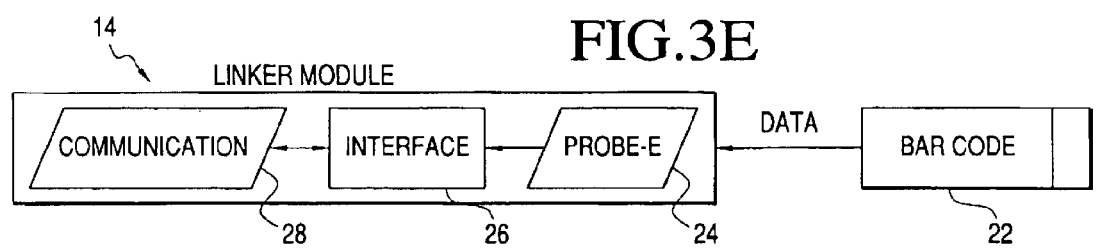
Figure 3F:
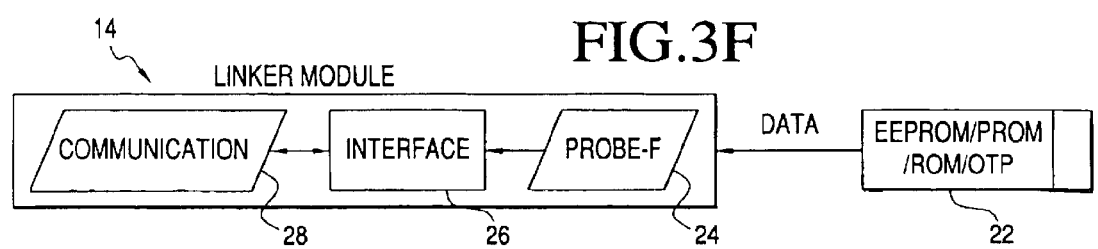

FIG. 3D shows use of a magnetic strip memory device. This magnetic strip would be similar to the strip provided on the rear of a credit card. A magnetic reader/writer head would scan and transfer data to and from the host system of the receiving station 16. A specialized interface module would be required to link the magnetic head to the communication module 28.

FIGS. 3E and 3F illustrate the use of a memory device having information therein capable of being read but not altered. For example, FIG. 3E shows use of a printable media such as a bar code or a dot code. In this instance, an optical reader would scan and transfer data to the receiving station 16. Therefore, an appropriate interface module is required to convert the data from the optical reader to the communication module.

Finally, FIG. 3F shows the use of an electrical programmable read-only memory (EPROM), read-only memory (ROM) as well as a one-time programmable memory (OTP). All of these memory devices allow information to be read from the memory, but this information could not be altered in any manner. All of the aforementioned memory devices can be provided in a form which is directly affixed to the drug chamber container 50. Alternatively, each of these memory devices can be provided in a portable form such as embodied or attached to a credit-type card. In this instance, the memory devices would travel with the patient and information would be read from these devices or entered into these devices at the receiving station 16 without the need of a modem to transfer the information from a remote site to the receiving station 16.

The linker unit 14 includes a probe 24, an interface module 26, as well as a communication module 28. The probe 24 is driven by the interface module 26 and is responsible to relay data between the memory device 22 and the interface module 26. Based upon the type of memory device 22 utilized, the type of probe 24 would be selected accordingly.

The interface module 26 is used to drive the probe and convert data between the probe and the communication module. Therefore, as can be appreciated, the probe 24 can be directly connected to the interface module 26 using an electrical connection or can be connected employing other types of communication links between the probe 24 and the interface module 26.

Various connections between the probe 24 and the interface module 26 based upon the types of memory employed in the system are illustrated in FIGS. 7A–7D. For example, when the communication module 28 is a modem and a touch memory device is employed, the data conversion would be from/to serial one wired format to serial RS-232 standard. It is noted that based upon the type of memory device 22 utilized, the type of probe 14 needed to read information from these memories would be chosen based upon the type of memory device employed.

The communication module 28 is used to transmit the converted information provided in the interface module 26 via a link to the receiving system 16. Based upon the type of link 18 utilized, the communication module 28 can take many different forms. Additionally, the communication module 28 can operate by wirelessly transmitting optical, infrared or similar waves to the receiving station 16. These types of linkages are illustrated with respect to FIGS. 6A–6E.

Furthermore, when the information provided in the memory 22 is converted to audible, subaudible tones or synthesized speech through the operation of the probe 24 and/or the interface module 26, these tones can be used to connect, transmit and receive data to/from any telephone hand set. This device would still require the interface module 26 to convert data from/to one wire standard to RS-232 serial or parallel information. When used in this manner, the linker unit 14 could be placed over the microphone of the telephone set and upon activation would read and dial a preprogrammed telephone number stored in the memory 22. When connection is established between the linker unit 14 and the receiving system 16, the unit 14 would securely transfer the appropriate data to the receiving system 16. When data is ready to be transmitted to the memory device 22, the user would then place the device over the telephone speaker and when transmission is confirmed, the call would be terminated. This device would be compact and portable and would not require a base unit or any attachments to function. The users could be patients or any other health personnel. This device would incorporate the appropriate reader for the type of memory unit 22. The device will have a visual and/or audible status indicator and would have the advantage of being utilized with any telephone set without any pre-installation.

Referring again to FIG. 7A, several possible conversions of the interface module are illustrated. The interface module 26 might convert the one wire date to parallel data if other communication devices are used. For example, if the interface module has an RS-232 input/output as an external port, an external cable would be required to connect the RS-232 port to the modem. The interface module could be mounted on the, printed circuit board of the modem. In this situation, the linker module 14 can be packaged as one device which includes a modem, an interface module as well as a reader/writer.

Figure 5:
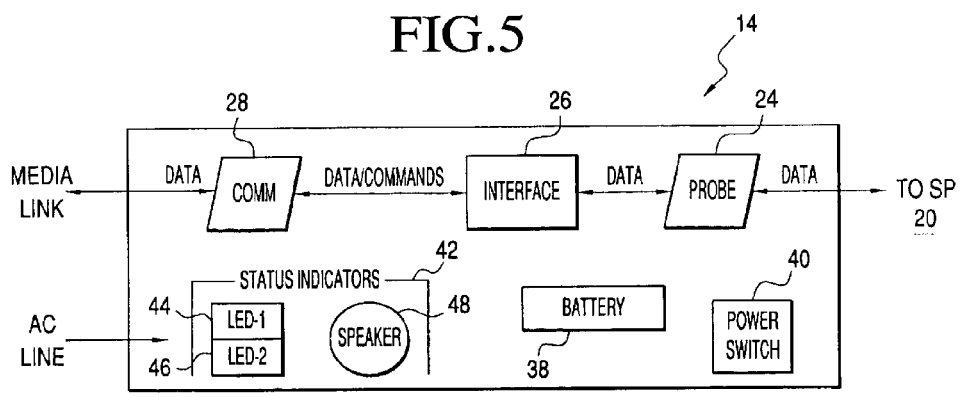
FIG. 5 is a block diagram showing the components of a linker module.
Figure 6A:
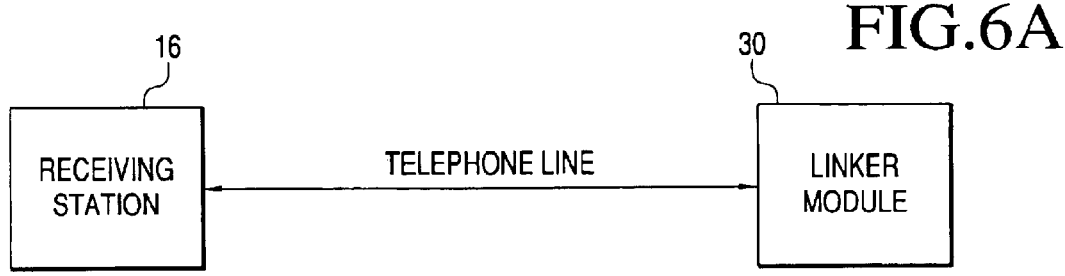
FIGS. 6A–6E are diagrams depicting various links between the linker module and a receiving station.
Figure 6B:
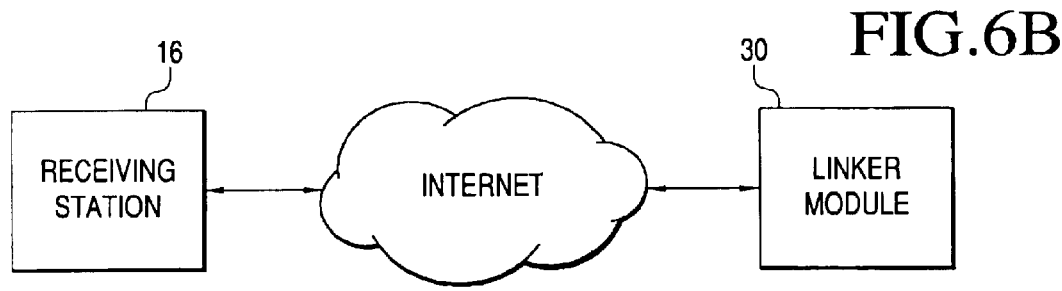
Figure 6C:
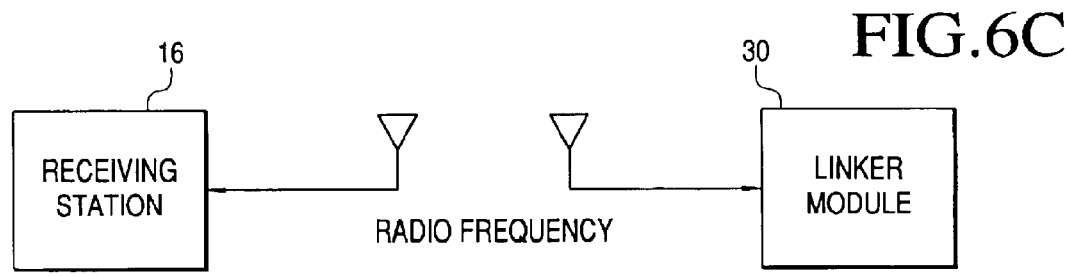
Figure 6D:
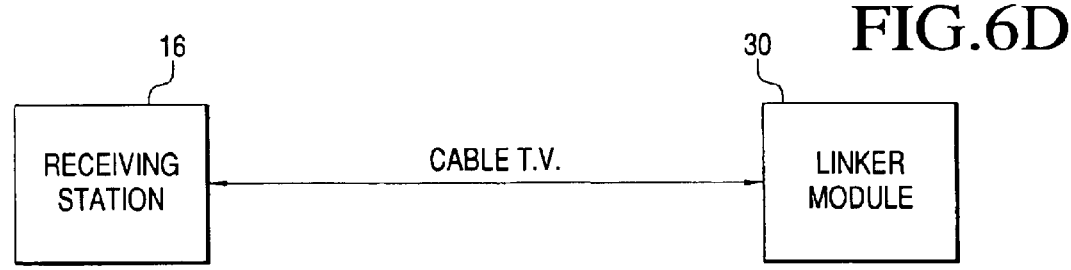
Figure 6E:
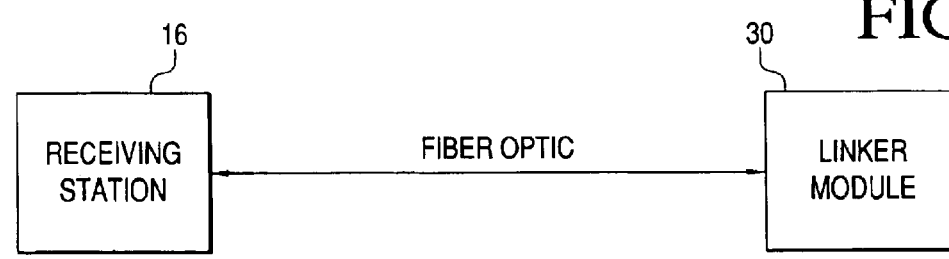
Figure 7A:
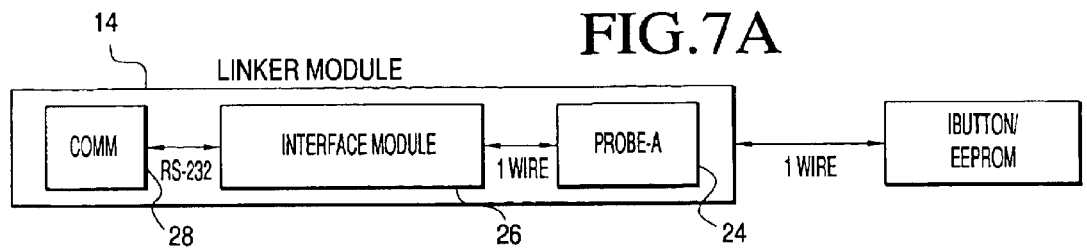
FIGS. 7A–7D are diagrams showing various connections between the linker module and the memory device.
Figure 7B:
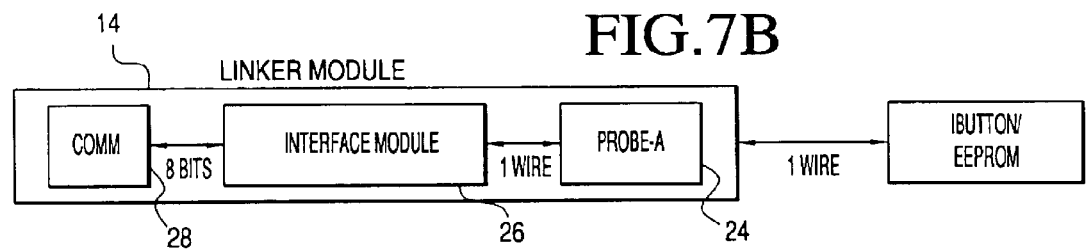
Figure 7C:
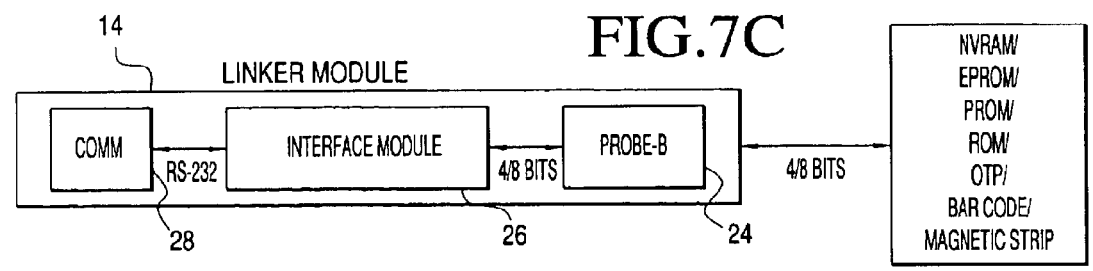
Figure 7D:
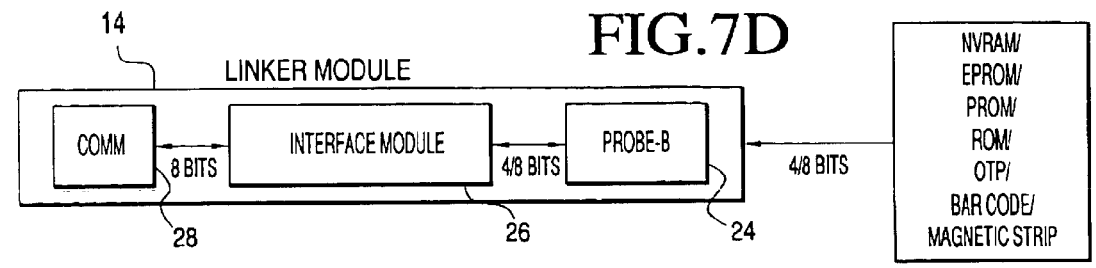

The linker module 14 can be a stand alone device as shown in FIG. 5. This device can be powered by an AC power line or by an internal battery source 38 connected directly or indirectly to a telephone line or similar media link. A power switch 40 would be included to turn the system on and off. One or more light emitting devices or similar types of indicators 44, 46 could be included to show the status of the linker module and the system as a whole. A speaker 48 could be included to provide audio outputs used to relay the status of the system to the user. Although FIG. 5 shows the probe 24 provided within the linker module 14, this need not be the case. Rather, the probe 24 can be provided outside of the linker module 14 and can be directly wired to the linker module 14 or can be provided with an electrical plug linkage. Alternatively, the communication between an external probe and the linker module 14 can be accomplished by a wireless communication system.

The receiving system 16 is linked to the linker unit 14 by the type of links shown in FIGS. 6A–6E. The receiving system 16 is composed of both hardware components operated by software. The receiving system 16 will be functional as a stand alone unit or part of a multi-systems network. The system has a network module to provide different manners of communication. This module will be capable of handling multiple communication protocols according to the link media 18. The system would have a secure means of authentication before allowing any data to be transferred from the receiving station 16, or into the receiving station 16. The system will keep log files of all communications. The system will have supervisory software as well as an error checking mechanism. The receiving system 16 could include its own database or be in communication with various other databases. These databases would be accessible to physicians, patients, pharmacists, management personnel and the like.

As previously discussed, the linker unit 14 is composed of a communication module, an interface module and a probe (reader/writer). The linker unit 14 functions to read or write data from and to the memory device 22 and to establish communication with a receiving system 16 for the purpose of transferring data between the receiving system 16 and the memory device 22. A modem would be used to link and to communicate information from the memory unit 22 to the receiving system 16 directly over telephone lines. A different module might be substituted for the modem when different types of links would be required or desired. The main function of the modem would be to dial the telephone number of the receiving system 16 and to establish communication between the communication module 28 and the receiving system 16. The main component of the interface module 26 would be a micro processor system to convert data from the one wire standard of the reader/writer or from/to the RS-232 standard signals when a touch memory would be employed.

Figure 8:
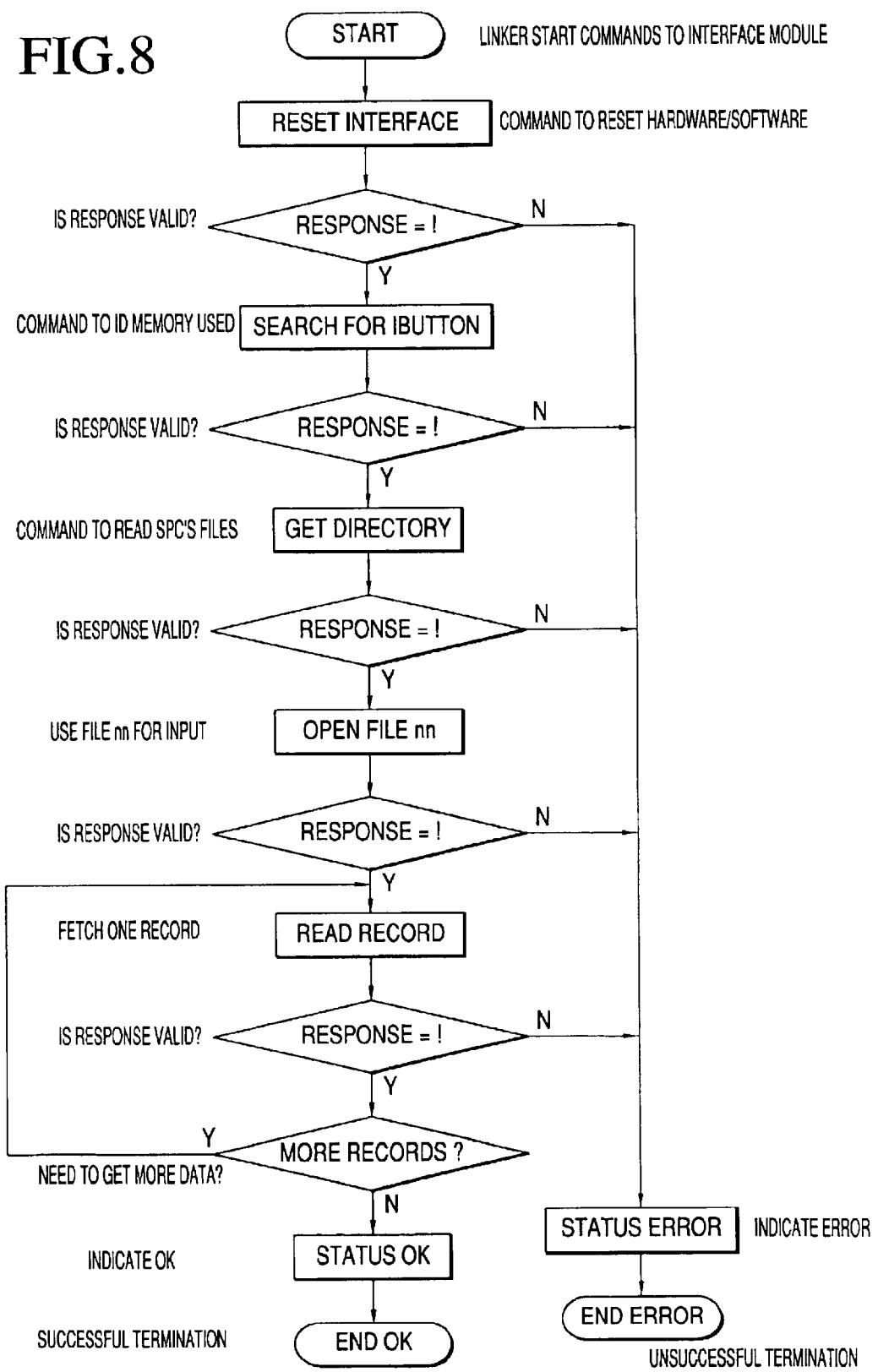
FIG. 8 is a flow diagram showing a method of reading the memory device.

FIGS. 8–11 illustrate flow diagrams used to read information from the memory device 22 and illustrate the operation of the linker module 14 as well as the receiving system 16. FIG. 8 depicts one of several methods of reading data from the memory device 22. More specifically, FIG. 8 illustrates the use of a touch memory (Ibutton) device for storing information. Linker module 14 would command the interface module 26 to begin communication with the probe 24 which is directly or indirectly in contact with the memory unit 22. The memory ID 52 of the touch memory unit is identified. If the proper response is received by the interface module, the interface module would then request information from one or more files 56, 58 and 60 of the memory directory 54 based upon information received by the linker unit 14 from the receiving system 16. One or more records of the various files would then be read from the memory device 22 and transmitted to the receiving system. Once one or more of the file records is read and transmitted to the receiving station, the reading step would be terminated.

The data stored in any types of memory units utilized or contemplated by the present invention can take many forms. For instance, this data includes but is not limited to the receiving systems, telephone number as well as the receiving stations Internet protocol (IP) address. Furthermore, the data would include the patient's identification number, the name, address, date of birth, and home telephone number of the patient or his representative. The data would also include the types of medications that the individual is taking as well as instructions relating to these medications and other important information. Furthermore, if information relating to allergies, the maximum dosage allowed, a prescription number, date, physician's name and telephone number, past medical history, statistical data for tracking and monitoring the patient as well as other relevant data could also be included in these memory devices.

The memory device 22 can be issued to the patient in many ways. For example, when a prescription is initially ordered, the memory device 22 including all pertinent information such as the number of refills would be directly attached to a medication container 50 such as shown in FIG. 2.

Figure 9:
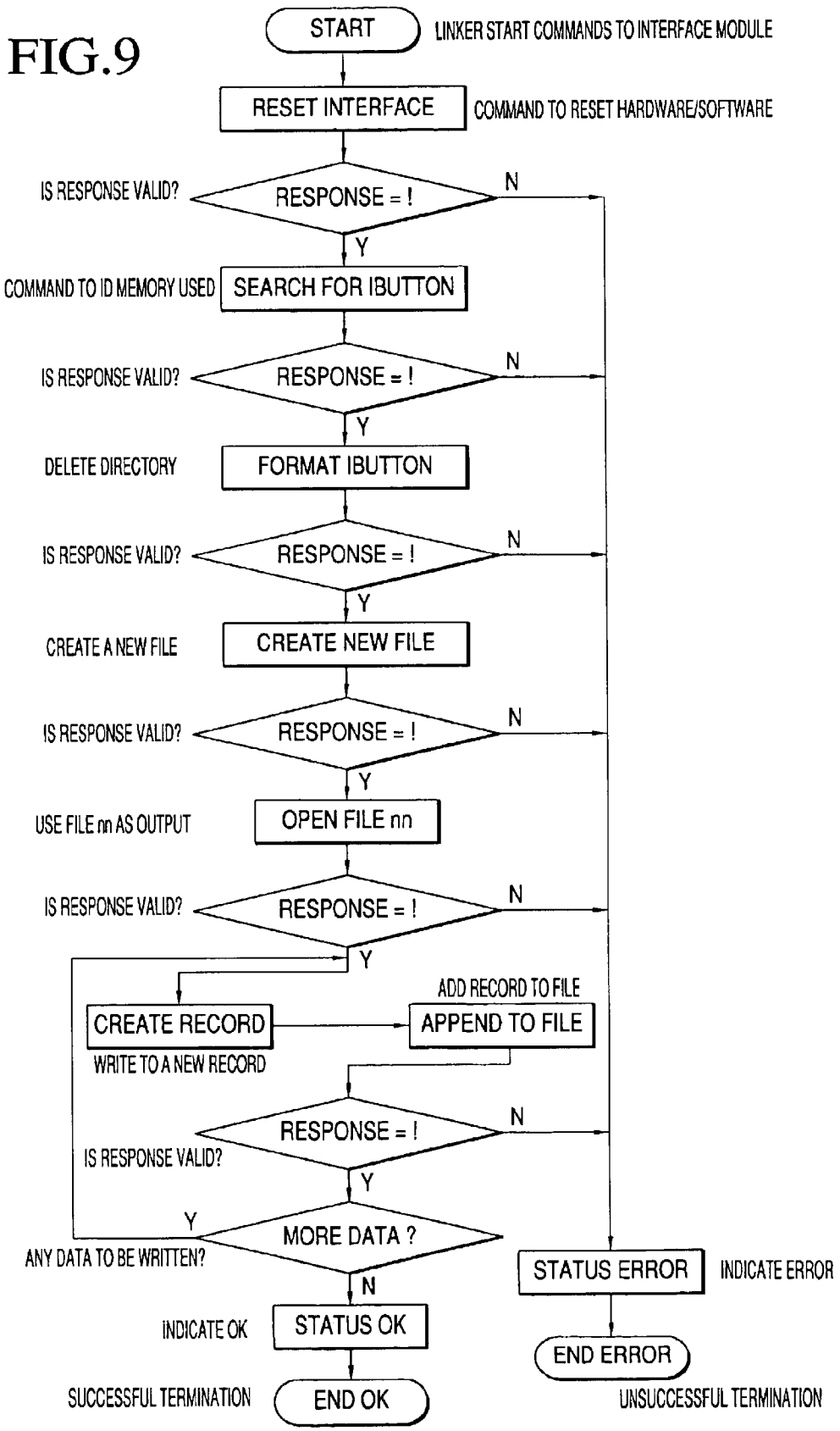
FIG. 9 is a flow diagram showing the procedure of writing information into the memory device.

FIG. 9 illustrates the writing function performed by the receiving system 16 either prior to reading the information contained in the memory device 22 or subsequent to reading information from the memory device 22. After the linker module 14 is connected to the receiving system 16, commands would be initiated to begin the writing operation. As shown in FIG. 9, new files can be created or the information provided in old files can be altered from the receiving system 16. Once all the information has been written in the proper locations of any of the memory devices 22 described or contemplated by the present invention, the writing step would be terminated. It is important to note that when this system is used to remotely refill prescriptions, the receiving system 16 might merely note that an additional refill of a particular medication has been authorized. In this instance, the patient or his representative could then, after the call to the pharmacy, be able to immediately pick up the medication once the prescription has been filled. Since some of the information provided in the different memory devices 22 relate to the patient's condition, it is noted that if the receiving system 16 is a physician's office, the physician or his representative could easily update the memory devices 22 by a simple phone call. Furthermore, the physician could prescribe additional medication to the individual by opening a new file or altering an old file. Once this is accomplished, the patient could then initiate a call to a remote pharmacy to fill this new prescription.

Figure 10:
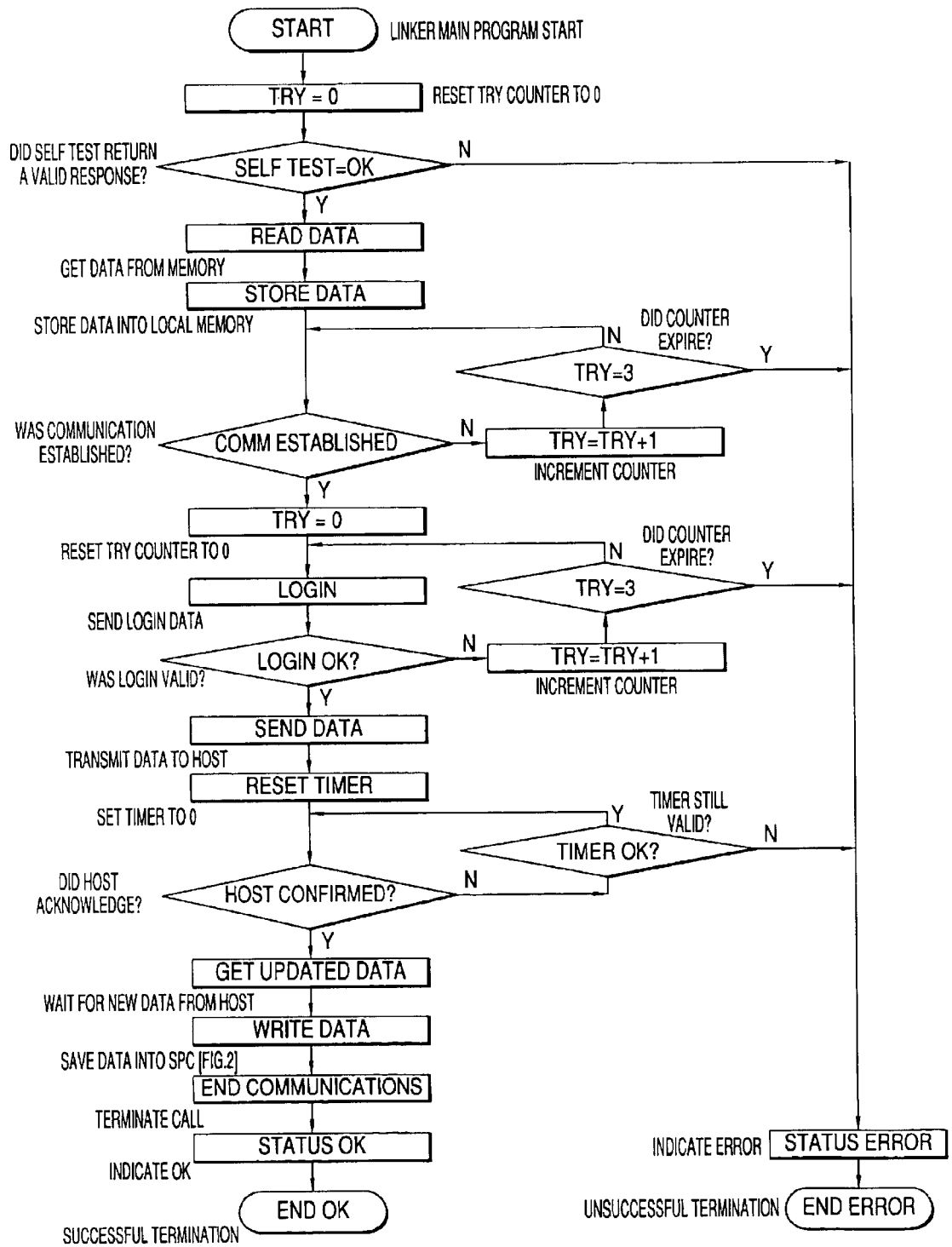
FIG. 10 is a flow diagram showing the operation of the linker module.

Referring now to FIG. 10 which illustrates the logical flow for the linker module 14, communication is established between the interface module 26 as well as the communication module 28. Once this communication has been confirmed, the linker module 14 can contact the receiving system as well as to read data from any of the memory units 22.

Figure 11:
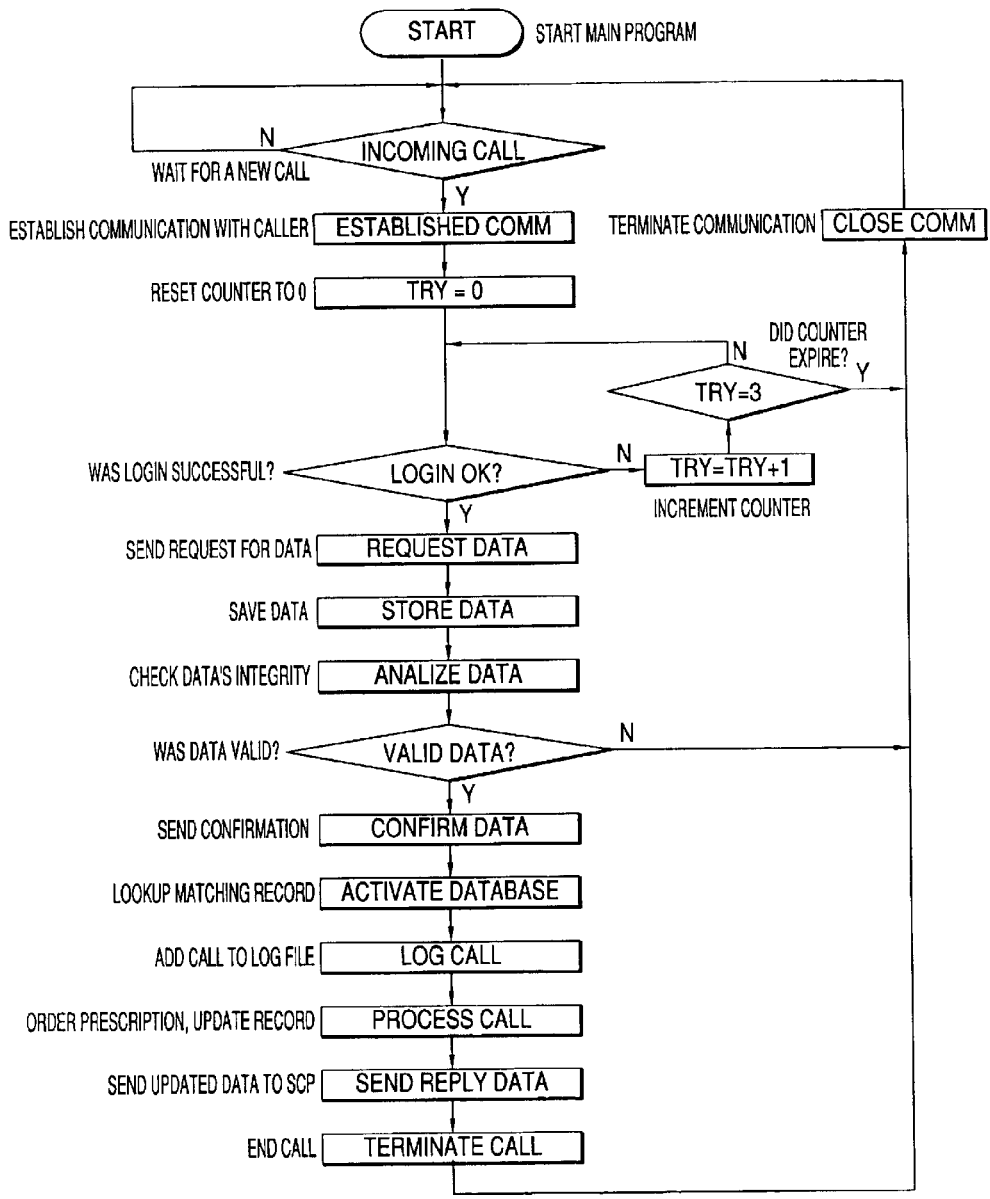
FIG. 11 is a flow diagram showing the operation of the receiver system.

FIG. 11 illustrates a flow diagram showing the operation of the receiving system 16. In use, the patient would place one of the memory devices 22 directly in contact with the probe 24 or at a location in which communication between the probe 24 and the specific memory unit 22 can be initiated. It is noted that the memory unit 22 can be directly affixed to drug chamber 50 or to be at a location isolated from any drug chamber. Once the probe 24 is in direct or indirect contact with the memory unit 22, the linker module 14 would become activated. This could occur automatically when the probe 24 and the memory unit 22 are linked, or it could be initiated by an "on/off" or similar activation device associated with the linker module 14. The linker module 14 would then perform a self-test. If the results of this self-test is positive, the linker module 14 through the probe 24 would begin to interrogate the memory device 22. The linker module 14 would then request from the memory device 22 to send its identification number. Once it is established that the identification number is proper, the linker module 14 would then request the memory device 22 to send some or all of the data stored therein. If this data is within the specification, this data would be stored on a solid state memory device provided within the linker module 14. The linker module would then establish communication with the receiving system as previously described. If communication was not established after one or more tries, the linker module 14 would indicate by one or more of the status indicators 44, 46 that the communication link between the linker module 14 and the receiving system 16 was not established.

Once a proper link between the receiving system and the linker module 14 was provided, the linker module would request data transfer to the receiving system 16. When this is granted, the data transferred from the memory device 22 to the linker module 14 would then be transferred to the receiving system 16 which would then confirm that a data transfer was completed. If this confirmation is not received from the linker module 14, one or more of the status indicators would indicate that no data transfer was confirmed.

The receiving system 16 would then process the received data and, if necessary, would transmit data from the receiving system 16 to the linker module 14. The linker module 14 would then send a confirmation to the receiving system that this data was received from the receiving system 16. Once all these communications are confirmed, the linker module 14 would terminate the communication with the receiving system 16.

The above-described system and method would benefit both the physician as well as a the patient. The physician would be able to alter a patient's prescription as needed and include modifications to a patient's prescription as well as a change in the medical status of the patient which can be directly added to any of the memory devices from a remote location. The patient can then contact a pharmacy at a remote location and request that a new prescription or a refill prescription be filled. The patient or his representative would then be able to easily and officially pick up the filled prescription or, in the alternative, the pharmacy would be able to deliver the medication to the patient.

The system can also be used in an interactive manner for monitoring patient drug use and/or for statistical analysis as well as a cost analysis. Since the information is automatically transferred from the memory device 22 to or from the host receiving system 16 mistakes can be prevented in filling prescriptions, particularly when the patient is elderly or is not particularly conversive in English.

Having described specific preferred embodiments of the invention with reference to the accompanying drawings, it is to be understood that the invention is not to be limited to those precise embodiments, and that various changes and modifications may be effected therein by one skilled in the art without departing from the scope or spirit of the invention and as defined in the appended claims.

What is claimed:

1. A system for an individual ordering or reordering medication from a location removed from the individual, the location provided with a receiving device and a device for filling or refilling a medication order based upon information directly transmitted to the receiving device, consisting of:

a container for holding medication;

a memory device directly attached to said container, said memory device provided with information relating to the individual and/or the medication; and a receiver provided at a location remote from the receiving device only for reading said information included in said memory device and for transmitting said information to the receiving device, said receiver generally non-contiguous with said container and said memory device.

2. The system in accordance with claim 1, further including a device for writing information into said memory device.

3. The system in accordance with claim 2 wherein said information provided within said memory device relates to the number of refills for a particular medication.

4. The system in accordance with claim 2 wherein said information written into said memory device relates to the number of refills for a particular medication.

5. The system in accordance with claim 1 wherein said information provided within said memory device relates to the number of refills for a particular medication.

6. The system in accordance with claim 1 wherein said information written into said memory device relates to the number of refills for a particular medication.

7. The system in accordance with claim 1, wherein said memory device is a solid state memory.

8. The system in accordance with claim 7, wherein said solid state memory is a touch memory device.

9. The system in accordance with claim 1, wherein said memory device is a magnetic strip provided on a base.

10. A method for an individual ordering or reordering medication from a location removed from the individual, the location provided with a receiving device and a device for filling or refilling a medication order based upon information directly transmitted to the receiving device, consisting of the steps of:

inputting information into a memory device relating to the individual and/or medication;

issuing said memory device to the individual;

attaching said memory device to a container;

reading said information from said memory device utilizing a reading device generally non-contiguous with said container, to only read said information from said memory device;

transmitting said information read by said reading device to the receiving device; and filling or refilling a medication order based upon said information directly transmitted to said receiving device from said reading device, said filling or refilling step completed at a location approximate with said receiving device.

11. The method in accordance with claim 10 further including the step of transmitting said information from said reading device to said receiving device over a telephone line.

* * * * *